(12) United States Patent
Knauf et al.

(10) Patent No.: US 7,763,759 B2
(45) Date of Patent: Jul. 27, 2010

(54) CONTINUOUS PROCESS FOR THE MANUFACTURE OF NITROBENZENE

(75) Inventors: Thomas Knauf, Dormagen (DE);
Alexandre Racoes, Krefeld (DE);
Wolfgang Dohmen, Duisburg (DE);
Andreas Rausch, Neuss (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/563,300

(22) Filed: Sep. 21, 2009

(65) Prior Publication Data

US 2010/0076230 A1  Mar. 25, 2010

(30) Foreign Application Priority Data

Sep. 24, 2008  (DE) ................. 10 2008 048 713

(51) Int. Cl.
*C07C 205/00* (2006.01)
(52) U.S. Cl. ........................................ 568/927
(58) Field of Classification Search ........... 568/927
See application file for complete search history.

(56) References Cited

U.S. PATENT DOCUMENTS

| | | | | |
|---|---|---|---|---|
| 2,256,999 A | | 9/1941 | Castner | |
| 4,973,770 A | * | 11/1990 | Evans | 568/929 |
| 5,616,818 A | * | 4/1997 | Pirkl et al. | 568/932 |
| 5,763,697 A | | 6/1998 | Hermann et al. | |
| 6,242,657 B1 | | 6/2001 | König et al. | |
| 6,562,247 B2 | | 5/2003 | Gillis et al. | |
| 7,326,816 B2 | | 2/2008 | Knauf et al. | |
| 2003/0055300 A1 | | 3/2003 | Chrisochoou et al. | |

FOREIGN PATENT DOCUMENTS

| | | |
|---|---|---|
| EP | 0373966 B1 | 10/1993 |
| EP | 0489211 B1 | 2/1996 |
| EP | 0436443 B1 | 4/1996 |
| EP | 0779270 B1 | 6/2000 |
| WO | 2009/002734 A1 * | 12/2008 |
| WO | 2009002734 A1 | 12/2008 |

* cited by examiner

*Primary Examiner*—Jafar Parsa
(74) *Attorney, Agent, or Firm*—N. Denise Brown; Noland J. Cheung

(57) ABSTRACT

The invention relates to a continuous process for the manufacture of nitrobenzene. This process comprises the nitration of benzene with nitrating acid that contains at least 3.0 wt. % of nitric acid and at least 67.0 wt. % of sulfuric acid, in a reaction space in which the start temperature of the reaction is above 100.0° C. but below 102.0° C. In addition, this process requires that the benzene and the nitrating acid are dispersed in one another several times.

5 Claims, No Drawings

CONTINUOUS PROCESS FOR THE MANUFACTURE OF NITROBENZENE

CROSS REFERENCE TO RELATED PATENT APPLICATION

The present patent application claims the right of priority under 35 U.S.C. §119 (a)-(d) of German Patent Application No. 102008048713.9, filed Sep. 24, 2008.

BACKGROUND OF THE INVENTION

The invention relates to a continuous process for the manufacture of nitrobenzene. This process comprises the nitration of benzene with a nitrating acid that contains at least 3.0 wt. % of nitric acid and at least 67.0 wt. % of sulfuric acid, in a reaction space in which the start temperature of the reaction is above 100.0° C. but below 102.0° C. In addition, the process requires that the benzene and the nitrating acid are dispersed in one another several times.

The present invention relates to a continuous process for the manufacture of nitrobenzene that essentially corresponds to the concept of the adiabatic nitration of benzene with a mixture of sulfuric and nitric acids (nitrating acid). Such a process was disclosed in U.S. Pat. No. 2,256,999 and current embodiments of this adiabatic nitration are now described in, for example, EP 0 436 443 B1, EP 0 771 783 B1 and U.S. Pat. No. 6,562,247. The processes with an adiabatic mode of reaction are particularly distinguished by the fact that heating or cooling energy fluxes do not flow over the outer surface of the reaction volume by means of technical measures.

A common feature of the adiabatic processes described above is that the starting materials, i.e. benzene and nitric acid, are reacted in a large excess of sulfuric acid. The sulfuric acid then takes up the evolved heat of reaction and the water formed in the reaction.

To carry out the reaction, nitric acid and sulfuric acid are generally mixed or dispersed to form so-called nitrating acid, and benzene is metered into this nitrating acid and reacts with the nitric acid to form substantially water and nitrobenzene. Benzene is used in at least the stoichiometric required amount, based on the amount of nitric acid, but preferably in a 2 to 10% excess, relative to the amount of benzene required by stoichiometry.

The reaction space in which benzene and nitric acid are reacted can consist of an arrangement of stirred tanks, a loop reactor or one or more tubular reactors connected in series or parallel. The tubular reactors can be of cylindrical or conical design. It is advantageous to operate the tubular reactors without back-mixing, so the magnitude of the flow rate inside the tubular reactor is chosen so that plug-flow behaviour is achieved over the whole of the reactor.

The dimensions of the reaction space are generally such that a reaction mixture substantially free of nitric acid is obtained after the reactants have flowed through it. To describe the course of the reaction in the reaction space, it is useful conceptually to subdivide the latter into a start zone, in which the emulsion of benzene and nitrating acid is first produced by dispersion and in which the reaction starts and the reactants are optionally redispersed several times, and an adjoining end zone, in which the reaction proceeds to almost complete conversion of the nitric acid. In this process, the start zone physically begins with the first dispersion of benzene and nitrating acid. It is again possible, if desired, conceptually to subdivide this zone into several zones. The physical and chemical processes in a nitration apparatus are described in detail in EP 0 708 076 B1.

Downstream of the end zone of the nitration reactor, the reaction mixture is generally fed into a phase separation apparatus, where two phases are formed; the first phase being crude nitrobenzene and the second phase waste acid which consists substantially of water and sulfuric acid. At the same time, gases—substantially nitrogen oxides, water vapor and benzene vapor—are evolved from the liquid phase in the phase separation apparatus. These gases are generally fed into an exhaust gas system.

The waste acid obtained in the phase separation apparatus is conventionally fed into a flash evaporator, where water is evaporated as the waste acid is expanded into the vacuum, thereby cooling and concentrating the waste acid. The adiabatic mode of nitrating benzene with nitrating acid has the advantage that the heat of the exothermic reaction is utilized to heat the waste acid to the point where the concentration and temperature in the flash evaporator can simultaneously be adjusted to those of the sulfuric acid before the admixing of nitric acid and benzene.

By way of impurities, the nitrobenzene obtained in the phase separation apparatus (so-called crude nitrobenzene) still contains sulfuric acid, water and benzene, as well as nitrophenols and dinitrobenzene, which are separated off by suitable work-up processes, e.g. washing and distillation steps. One possible embodiment of this work-up is described in, for example, EP 1 816 117 A1.

Features of the adiabatic nitration of aromatic hydrocarbons are firstly that the temperature of the reaction mixture increases in proportion with the progress of the reaction, i.e. with the nitric acid conversion. Secondly, this creates a difference between the temperature of the mixed educts before the onset of the reaction (hereafter described as the start temperature) and the temperature of the reaction mixture after at least 99% nitric acid conversion (hereafter described as the reaction end temperature). Those skilled in the art are aware that, in general, the variable described here as the start temperature can advantageously be measured immediately after the benzene has been metered into the nitrating acid, i.e. before the first dispersion, and the variable described here as the reaction end temperature can be measured in the inlet of the phase separation apparatus. The difference between the start temperature and reaction end temperature depends on the type of hydrocarbon being nitrated and on the volumetric proportions in which the aromatic hydrocarbon and the nitrating acid have been used. A high volumetric ratio of aromatic hydrocarbon to nitrating acid (also called the phase ratio) gives a large temperature difference and has the advantage that a large amount of aromatic hydrocarbon is converted per unit time.

In industrial practice, such as in the case of the nitration of benzene, the reaction end temperature is limited by safety criteria to approx. 135 to 145° C., with the decisive role being determined by factors such as the thermal decomposition of the products and the vapor pressure of the product mixture, and hence the temperature and quantity of the exhaust gas. In view of this prescribed upper limit, it has previously seemed obvious to choose the lowest possible start temperature because this increases the difference relative to the reaction end temperature applicable on the industrial scale, and it becomes possible to achieve high space-time yields.

The most important criterion for describing the quality of an adiabatic process for the nitration of aromatic hydrocarbons is the end product's content of undesirable reaction by-products formed by multiple nitration or oxidation of the aromatic hydrocarbon or the nitroaromatic. In the case of the nitration of benzene, discussion always centers on the content of dinitrobenzene and nitrophenols, especially trinitrophenol (picric acid), which is to be classified as particularly explosive.

In order to obtain nitrobenzene with particularly high selectivities, the nature of the nitrating acid to be used has been determined in detail (see, for example, EP 0 373 966 B1, EP 0 436 443 B1 and EP 0 771 783 B1), and numerous suggestions have been put forward as to how the first mixing and the repeat mixing (redispersion) of benzene with the nitrating acid can be carried out (see EP 0 373 966 B1, EP 0 489 211 B1, EP 0771 783 B1, EP 0 779 270 B1, EP 1 291 078 A2 and U.S. Pat. No. 6,562,247). It has also been pointed out that the content of by-products is determined by the magnitude of the end temperature (cf. EP 0 436 443 B1, column 15, lines 22-25), that a high initial conversion is advantageous for a high selectivity, and that this is achieved when the intermixing effected at the beginning of the reaction is optimal (EP 0 771 783 B1, paragraph 0014). In EP 0 771 783 B1, the required intermixing is achieved by means of a rotating propulsive jet. The use of dispersing elements, as described in, for example, EP 0 489 211 B1 and EP 0 436 443 B1, is regarded in EP 0 771 783 B1 as unsuitable (see paragraphs 0012 to 0015).

All the cited processes are capable of producing nitrobenzene by the nitration of benzene with nitrating acid, an adiabatic mode of operation being used in order to heat the sulfuric acid with the heat of reaction and thereby be able to use the heat of reaction to concentrate the waste acid. All the processes described are capable of producing a crude nitrobenzene having a low content of by-products, i.e. containing only between 100 and 300 ppm of dinitrobenzene and between 1500 and 2500 ppm of nitrophenols, with it being possible for picric acid to make up 10 to 50% of the nitrophenols.

Furthermore, irrespective of this, the purity of the crude nitrobenzene is of decisive importance for industrial production. However, against the background of the increasing demand for nitroaromatics, especially for the manufacture of aromatic amines and aromatic isocyanates, there is another objective, namely to provide the possibility of manufacturing large amounts of these compounds in reaction equipment of maximum compactness.

The extensive state of the art scarcely goes into the dimensions of the proposed mixing equipment and reactors. Only EP 0 779 270 B1, however, gives concrete numerical data for a laboratory reactor.

One parameter for describing the ratio between the quantity which can be produced and the size of the reaction equipment is the space-time yield. This is calculated as the quotient of the producible quantity of target compound per unit time and the volume of the reaction equipment. In the present case of the nitration of benzene, the space-time yield is usefully calculated as the quotient of the nitrobenzene production in metric tons per hour and the volume of the reaction space, the latter being defined as the space which begins with the first dispersion of benzene and nitrating acid and within which the reaction proceeds to at least 99% completion. The residence time of the reaction mixture (consisting of aromatic compound and nitrating acid) within the reaction space is the reaction time.

$$\text{space-time yield } [t/m^3h] = \text{quantity produced } [t/h] / \text{reaction space } [m^3]$$

A high space-time yield is advantageous for the industrial application of a process because it makes it possible to construct compact reaction equipment distinguished by a low volume of investment relative to capacity.

The aim of the present invention is thus to provide a process which on the one hand affords a high space-time yield, and on the other hand continues to assure the required product quality.

It has surprisingly been found that the space-time yield can only be significantly increased, while maintaining product quality, when all the reaction-accelerating factors, i.e. the composition of the nitrating acid, the start temperature and the quality of the intermixing, are coordinated in such a way that, at the beginning of the reaction in a start zone making up at most 13 vol. % of the reaction space, at least 60% of the nitric acid used reacts with benzene to form nitrobenzene.

To increase the space-time yield, the state of the art makes provision for increasing the phase ratio and lowering the start temperature in order to obtain a greater difference relative to the reaction end temperature applicable on the industrial scale. It has been surprisingly found, however, that these measures, while increasing the space-time yield for nitrobenzene, are not capable of also maintaining the required product quality and the required process control.

To achieve space-time yields of more than 5 $t/m^3h$ while maintaining product quality, it is necessary to resort to two essential measures compared with a process according to the state of the art:

1. Raising the start temperature. This inevitably implies a higher reaction end temperature; however, when applying the combination of measures described here, this makes only a negligible contribution to the effect described in EP 0 436 443 B1, namely an increase in the content of by-products.
2. The reaction mixture must be redispersed several times at short intervals immediately after benzene has been metered in. If the dispersion frequency exceeds a preferred value of $\frac{1}{5}$ $s^{-1}$, i.e. if there is on average a period (corresponding to a residence time) preferably of more than 5 seconds between two (re)dispersions, increasing the space-time yield to more than 5 $t/m^3h$ leads to an impairment of product quality.

Surprisingly, it has been found that, by applying both the above measures, neither raising the start temperature alone (Comparative Example 1) nor increasing the dispersion frequency alone (Comparative Example 2) makes it possible to guarantee the manufacture of nitrobenzene with a space-time yield of 5.1 $t/m^3h$. In both cases the values of important process parameters, such as exhaust gas temperature and nitric acid conversion, are above or below the limiting values. It is only when both measures are combined in such a way as to satisfy the criterion according to the invention, i.e. namely at least 60% nitric acid conversion in a start zone making up at most 13 vol. % of the reaction space, that nitrobenzene can be produced with a space-time yield of more than 5 $t/m^3h$. (See Example 1 according to the invention). If the composition of the nitrating acid is additionally optimized, the space-time yield can also be increased to well above 5 $t/m^3h$. (See Example 2 according to the invention).

SUMMARY OF THE INVENTION

The invention relates to a continuous process for the manufacture of nitrobenzene by (1) nitrating benzene with nitrating acid in a reaction space in which benzene and the nitrating acid are dispersed in one another several times, characterized in that:

a) the nitrating acid used contains at least 3.0 wt. % of nitric acid and at least 67.0 wt. % of sulfuric acid, preferably 3.0 to 5.0 wt. % of nitric acid and 67.0 wt. % to 75.0 wt. % of sulfuric acid, with the wt. %'s in each case being based on 100 wt. % of the nitrating acid;

b) the start temperature of the reaction is above 100.0° C. but below 102.0° C., preferably at least 100.2° C. and preferably less than or equal to 101.5° C.;

c) the emulsion of nitrating acid and benzene obtained after the first dispersion is redispersed at least 4 times, preferably 4 to 8 times, before the nitric acid conversion is 60%, and d) at least 60% of the nitric acid used is converted within the first 13 vol. %, preferably within the first 1 to 13 vol. %, and more preferably within the first 5 to 13 vol. %, of the reaction space after the first dispersion.

The process according to the invention makes it possible to achieve a space-time yield of at least 5 tons of nitrobenzene per cubic meter of reaction space per hour. In one preferred embodiment of the process according to the invention, a space-time yield of nitrobenzene of over 5 t/m³h is achieved for the nitration of benzene in a tubular reactor with dispersing elements. This preferred embodiment is characterized by the following additional measures:

1) the nitrating acid used contains more than 3.0 wt. % of nitric acid and more than 67.0 wt. % of sulfuric acid, with the wt. %'s in each case being based on 100 wt. % of the nitrating acid; and 2) the nitration reactor is operated adiabatically, i.e. without technical measures for producing heating or cooling energy fluxes on its outer surface.

A good intermixing is advantageous for the reaction, so it is preferable to use a tubular reactor which has several dispersing elements distributed over its length. These dispersing elements assure an intimate intermixing and redispersion of benzene, nitric acid and sulfuric acid, and water.

A suitable reactor for the present process and the shape of dispersing elements which can be used herein are described in, for example, EP 0 489 211 B1, EP 0 708 076 B1 and EP 1 291 078 A2, which are believed to correspond to U.S. Pat. No. 4,994,242, U.S. Pat. No. 5,616,818 and U.S. Published Patent Application 20030055300, respectively, the disclosures of which are hereby incorporated by reference, or in the article "Recent advances in the technology of mononitrobenzene manufacture" (Guenkel, A. A.; Maloney, T. W., ACS Symposium Series, 623, Nitration (1996): 223-233). Guenkel and Maloney present a tubular reactor whose nine dispersing elements are evenly distributed over its length and consists of several perforated half-shells.

EP 1 291 078 A2, believed to correspond to U.S. Published Patent Application 20030055300, describes a tubular reactor having 3 to 11 tantalum dispersing elements which each create a pressure loss of 0.5 to 4 bar and each have 10 to 25 apertures for a mass flux of 1 t/h. The apertures can be slots, holes or perforations. In the process according to the invention, these parameters can also be put into effect in order to avoid phase coalescence and to keep the diameter of the organic droplets in the acid phase small. In this case the dispersing elements are designed in such a way that the mean droplet diameter is preferably smaller than 200 μm, and more preferably smaller than 120 μm.

An alternative preferred embodiment of the process according to the invention is characterized by the following additional measures:

1) the nitrating acid used contains more than 3.0 wt. % of nitric acid and more than 67.0 wt. % of sulfuric acid, with the wt. %'s in each case being based on 100 wt. % of the nitrating acid; and 2) part of the heat of reaction produced during the nitration, preferably in the region of the first 13 vol. % and more preferably within the first 20 vol. % of the reaction space after the first dispersion, is dissipated by cooling.

This has the effect of dissipating part of the heat of reaction, thereby lowering the reaction end temperature. The space-time yield can be further increased by means of the external reactor cooling until the reaction end temperature returns to the technically permissible limiting value.

The required reactor cooling can be effected by air cooling, by a heat exchange apparatus or, more preferably, by jacket cooling with a heat transfer medium. The heat of reaction is preferably dissipated in the region of the reactor where the reaction, i.e. the evolution of heat, principally occurs. In the process according to the invention, this region is the start zone and the immediately adjoining reaction space, i.e. cooling is carried out preferably in the region of the first 20 vol. % and more preferably within the first 15 vol. % of the reaction space after the first dispersion.

External cooling is preferably used only to a certain extent because it is crucial for the present invention that the nitric acid conversion is at least 60% at the end of the start zone. It is therefore preferable for cooling to be carried out only in the region of the first 20 vol. % and more preferably only within the first 15 vol. % of the reaction space after the first dispersion, it being possible for this cooling to extend over the entire region of the first 20 vol. % or 15 vol. % of the reaction space. However, it can also extend only over parts of said region such as, for example, only over the region from 0 to 13 vol. % or over the region from 2 to 13 vol. % of the reaction space.

It has been shown in a basic experiment that after a lowering of the reaction end temperature by half a degree Celsius, the space-time yield can be increased by 0.1 t/m³h until the reaction end temperature returns to its value without the use of cooling (see Comparative Example 5). This basic experiment shows that, in principle, the use of external cooling makes it possible to increase the space-time yield without adversely affecting product quality.

In Example 6 which is representative of the present invention, this observation was theoretically applied to an experiment which used a nitrating acid containing more than 3.0 wt. % of nitric acid and more than 67.0 wt. % of sulfuric acid. By including effective cooling it is even possible to achieve space-time yields of 6 t/m³h.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

1. Comparative Example 1 with Raised Start Temperature

Benzene in 7% stoichiometric excess was metered into a nitrating acid consisting of 3.1% of nitric acid, 67.2% of sulfuric acid and 29.7% of water. The amount of benzene was chosen so as to give a space-time yield of 5.1 tons/m³h, based on the reaction space. The mixture obtained was introduced at a start temperature of 101.4° C. into a reactor in which 99.25% of the nitric acid was reacted. Only 3 redispersions were effected by means of tantalum baffles within the first 13 vol. % of the reaction space after the first dispersion. The temperature measured after 10.9% of the reaction space was 116.6° C. The temperature difference of 15.2° C. corresponded to 49.2% of the temperature rise observed for a reaction end temperature of 132.3° C.

The temperature rise and nitric acid conversion were proportional to one another, so the nitric acid conversion after 10.9% of the reaction space was also 49.2%. After the reaction mixture had passed through the reactor, the reaction mixture was fed into a phase separation apparatus, where the exhaust gas was evolved at a temperature of 66.8° C. This temperature corresponded to a quantity of exhaust gas whose high $NO_x$ content makes it intolerable over a prolonged period from the point of view of safety and the environment. A permanent operation and further increases in pollution are not recommended for this quantity of exhaust gas.

2. Comparative Example 2 with Improved Reactor Having Increased Dispersion

The apparatus used was the same as that used in Example 1 except that 4 redispersions were effected by means of tantalum baffles within the first 13 vol. % of the reaction space after the first dispersion. To incorporate the fifth dispersing element, the reactor was shortened by 2.5 vol. % of the reactor volume at the end of the end zone and lengthened by 2.5 vol. % of the reactor volume at the beginning of the start zone, such that the overall reactor volume remained the same.

Benzene was reacted with nitrating acid in the same way as in Comparative Example 1. In contrast to Comparative Example 1, the start temperature was only 100.0° C. After 13.4 vol. % of the reaction space, the temperature of the reaction mixture was 118.3° C. The temperature difference of 18.3° C. corresponded to 58.5% of the temperature rise observed for a reaction end temperature of 131.3° C. The nitric acid conversion downstream of the start zone (i.e. in this case after the first 13 vol. % of the reaction space after the first dispersion) was 58.5% and the conversion downstream of the entire reactor was only 99.07%. After the reaction mixture had passed through the reactor, the reaction mixture was fed into a phase separation apparatus, where the exhaust gas was evolved at a temperature of 46.8° C. The sulfuric acid flowing out of the phase separation apparatus was concentrated in a flash evaporator, where the condensate separated off still contained 0.06 wt. % of nitric acid. This was 0.2% of the nitric acid used and represents an unjustifiably high loss of nitric acid.

3. Example 3 According to the Invention

The reactor described in Comparative Example 2 was used. Benzene was reacted with nitrating acid in the same way as in Comparative Examples 1 and 2. To ensure the production of nitrobenzene with a space-time yield of over 5 t/m³h without compromising quality, a start temperature of 101.4° C. was used in Example 3. After 13.4 vol. % of the reaction space, the temperature of the reaction mixture was 120.6° C. The temperature difference of 19.2° C. corresponded to 62.1% of the temperature rise observed for a reaction end temperature of 132.3° C. The nitric acid conversion in the start zone (i.e. in this case after the first 13 vol. % of the reaction space after the first dispersion) exceeded 60%; the conversion was 62.1% downstream of the start zone and 99.38% downstream of the entire reactor. After the reaction mixture had passed through the reactor, the reaction mixture was fed into a phase separation apparatus, where the exhaust gas was evolved at a temperature of 46.5° C. All the process parameters can be controlled without problems.

4. Example 4 According to the Invention

The reaction was carried out in the same reactor as that described above in Example 3, which was also representative of the invention. This time, however, the target space-time yield was 5.7 t/m³h. This was achieved by adjusting the start conditions such that the nitric acid conversion downstream of the start zone was over 60%. This was done by adjusting the sulfuric acid concentration to 67.0 wt. % and the start temperature to 100.2° C. After 13.4 vol. % of the reaction space, the temperature of the reaction mixture was 122.0° C. The temperature difference of 21.8° C. corresponded to 62.1% of the temperature rise observed for a reaction end temperature of 135.3° C. The nitric acid conversion in the start zone (i.e. in this case after the first 13 vol. % of the reaction space after the first dispersion) exceeded 60%; the conversion was 62.1% downstream of the start zone and 99.35% downstream of the entire reactor. After the reaction mixture had passed through the reactor, the reaction mixture was fed into a phase separation apparatus, where the exhaust gas was evolved at a temperature of 65.5° C. All the process parameters can be controlled without problems.

By suitably combining the reaction-accelerating factors of dispersion, sulfuric acid concentration and start temperature, Examples 3 and 4 which are representative of the present invention make it possible to meet the criterion according to the invention of at least 60% nitric acid conversion within the first 13 vol. % of the reaction space after the first dispersion of benzene and nitrating acid, and thus to manufacture nitrobenzene of the requisite quality with a space-time yield of over 5 t/m³h.

Table 1 shows the composition of the crude nitrobenzene phase in the separation apparatus of Comparative Examples 1 and 2 and of Examples 3 and 4 according to the invention, together with the temperatures along the reactor and the exhaust gas temperature. The same reactor volume was used in all four Examples and the sulfuric acid concentrations used are indicated in the table.

TABLE 1

Experiments to obtain space-time yields of more than 5 t/m³h

|  | Comparative Example 1 | Comparative Example 2 | Example 3 according to the invention | Example 4 according to the invention |
|---|---|---|---|---|
| Space-time yield of nitrobenzene (t/m³h) | 5.1 | 5.1 | 5.1 | 5.7 |
| Total number of dispersions in start zone | 4 | 5 | 5 | 5 |
| Sulfuric acid concentration in nitrating acid (wt. %) | 67.20 | 67.05 | 67.10 | 67.00 |
| Nitric acid concentration in nitrating acid (wt. %) | 3.1 | 3.2 | 3.2 | 3.5 |

TABLE 1-continued

Experiments to obtain space-time yields of more than 5 t/m³h

|  | Comparative Example 1 | Comparative Example 2 | Example 3 according to the invention | Example 4 according to the invention |
|---|---|---|---|---|
| Start temperature (° C.) | 101.4 | 100.0 | 101.4 | 100.2 |
| Temperature downstream of start zone (° C.) | 116.6 | 118.3 | 120.6 | 122.0 |
| Reaction end temperature (° C.) | 132.3 | 131.9 | 132.3 | 135.3 |
| Nitric acid conversion downstream of start zone (%) | 49.2 | 58.5 | 62.1 | 62.1 |
| Nitric acid conversion downstream of end zone (%) | 99.25 | 99.07 | 99.38 | 99.35 |
| Exhaust gas temperature (° C.) | 66.8 | 46.8 | 46.5 | 65.5 |
| Total nitrophenols (ppm) | 2086 | 2100 | 2079 | 2127 |
| Picric acid (ppm) | 288 | 354 | 239 | 306 |
| Dinitrobenzene (ppm) | 153 | 182 | 201 | 224 |
| Note | exhaust gas temperature close to limiting value | low nitric acid conversion | no problems | no problems |

5. Comparative Example 5

Influencing the External Reactor Cooling

The reaction Was carried out in the same reactor as that described above in Examples 3 and 4 which are representative of the present invention. Benzene in 7% stoichiometric excess is metered into a nitrating acid consisting of 2.3 wt. % of nitric acid, 68.0 wt. % of sulfuric acid and 29.7 wt. % of water. The amount of benzene was chosen so as to give a space-time yield of nitrobenzene of 4.3 t/m³h, based on the reactor volume. The mixture obtained was introduced into a reactor at a start temperature of 99.8° C. After 13.4 vol. % of the reaction space, the temperature of the reaction mixture was 113.6° C. The reaction end temperature was 123.6° C.

The external reactor cooling was now applied, being located downstream of the start zone but within the first 15 vol. % of the reaction space after the first dispersion. The effect of applying the external cooling was to lower the reaction end temperature by 0.5° C. to 123.1° C. The load was increased in steps until the reaction end temperature returns to its value before the use of external cooling. This temperature was regained at a space-time yield of 4.4 t/m³h. As shown by the analytical values in Table 2, a crude nitrobenzene of the same quality was now obtained at the same reaction end temperature despite a higher space-time yield.

Even when this basic experiment was carried out with space-time yields of less than 5 t/m³h, it nevertheless showed that correct positioning and measured application of the external cooling enables the space-time yield to be increased without having to compromise product quality or the nitric acid conversion.

6. Example 6 According to the Invention

Influencing the External Reactor Cooling (Simulation)

As in Comparative Example 5, reactions with and without external cooling are compared with one another. The data underlying this Example were calculated.

If the nitration of benzene is carried out in a tubular reactor as described in Example 2, according to the criteria of the present invention with a space-time yield of 6.0 t/m³h, benzene in 7% stoichiometric excess is introduced into a nitrating acid consisting of 3.7 wt. % of nitric acid, 67.0 wt. % of sulfuric acid and 29.3 wt. % of water. A start temperature of 101.5° C. is adopted for the mixture obtained. The reaction enthalpy and the composition of the reaction mixture result in a reaction end temperature of 137.3° C. The nitric acid conversion after 13 vol. % of the reaction space can be calculated as 67.0%.

With a reaction end temperature of 137.3° C., a large quantity of exhaust gas is to be expected during the manufacture of nitrobenzene, and this is not permanently acceptable without additional technical measures.

On the other hand, the use of efficient external reactor cooling can lower the reaction end temperature by, for example, 3° C. If the cooling is effected downstream of the start zone but within the first 15 vol. % of the reaction space after the first dispersion, the nitric acid conversion in the start zone remains unchanged. Hence, correct positioning of the external cooling assures production with high space-time yields, but still allows high nitric acid conversions in the start zone.

Table 2 shows the composition of the crude nitrobenzene phase in the separation apparatus of Comparative Example 5, together with the temperatures along the reactor. The term 'start zone' (as used previously in Examples 1 to 4) again denotes the first 13 vol. % of the reaction space after the first dispersion.

TABLE 2

Experiments with and without external reactor cooling

|  | Comparative Example 5 | | Example 6 according to the invention - Simulation | |
|---|---|---|---|---|
|  | without cooling | with cooling | without cooling | with cooling |
| Space-time yield of nitrobenzene (t/m³h) | 4.3 | 4.4 | 6.0 | |
| Number of dispersions in start zone | 5 | | 5 | |
| Sulfuric acid concentration in nitrating acid (wt. %) | 68.0 | 68.0 | 67.0 | |
| Nitric acid concentration in nitrating acid (wt. %) | 2.27 | 2.30 | 3.71 | |
| Start temperature (° C.) | 99.8 | | 101.5 | |
| Temperature downstream of start zone (° C.) | 113.6 | 114.1 | 125.5 | 125.5 |
| Reaction end temperature (°C) | 123.6 | 123.6 | 137.3 | 134.3 |
| Nitric acid conversion downstream of start zone (%) | 58.2 | 60.1 | 67.0 | 67.0 |
| Nitric acid conversion downstream of end zone (%) | 99.44 | 99.45 | 99.6 | 99.6 |
| Total nitrophenols (ppm) | 1915 | 1900 | — | — |
| Picric acid (ppm) | 195 | 191 | — | — |
| Dinitrobenzene (ppm) | 140 | 138 | — | — |

Although the present invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for the manufacture of nitrobenzene comprising
   (1) nitrating benzene with a nitrating acid in a reaction space in which said benzene and said nitrating acid are dispersed in one another several times, wherein:
      a) said nitrating acid contains at least 3.0 wt. %, based on 100 wt. % of said nitrating acid, of nitric acid and at least 67.0 wt. % of sulfuric acid, based on 100 wt.% of said nitrating acid;
      b) the starting temperature of the reaction is above 100.0° C. but below 102.0° C.;
      c) the emulsion of said nitrating acid and said benzene which is obtained after the first dispersion is redispersed at least 4 times before the nitric acid conversion is 60%;
      and
      d) at least 60% of said nitric acid used is converted within the first 13 vol. % of the reaction space in the direction of flow of the reactants after the first dispersion.

2. The process of claim 1, wherein said nitration is carried out without heating or cooling.

3. The process of claim 1, wherein said nitration is cooled in the region of the first 20 vol. % of the reaction space in the direction of flow of the reactants.

4. The process of claim 1, wherein said nitration is cooled in the region of the first 15 vol. % of the reaction space in the direction of flow of the reactants.

5. The process of claim 1, wherein the resultant nitrobenzene is produced with a space-time yield of more than 5 tons per cubic meter of reaction space per hour.

* * * * *